United States Patent [19]

Phuc

[11] Patent Number: 4,788,974
[45] Date of Patent: Dec. 6, 1988

[54] HIGH-FREQUENCY ARTIFICIAL RESPIRATOR

[75] Inventor: Tran N. Phuc, Ohmiya, Japan

[73] Assignee: Senko Medical Instrument Mfg. Co., Ltd., Tokyo, Japan

[21] Appl. No.: 145,633

[22] PCT Filed: Nov. 21, 1985

[86] PCT No.: PCT/JP85/00646
§ 371 Date: Jul. 14, 1986
§ 102(e) Date: Jul. 14, 1986

[87] PCT Pub. No.: WO86/03128
PCT Pub. Date: Jun. 5, 1986

Related U.S. Application Data

[63] Continuation of Ser. No. 890,020, Jul. 14, 1986, abandoned.

[30] Foreign Application Priority Data

Nov. 22, 1984 [JP] Japan .................. 59-177474
Apr. 5, 1985 [JP] Japan .................. 60-50807

[51] Int. Cl.⁴ .......................................... A61M 16/00
[52] U.S. Cl. .......................... 128/204.21; 128/204.25
[58] Field of Search .................. 128/204.21, 204.23, 128/204.24, 204.25, 204.26, 205.13, 205.14, 205.15, 205.16, 205.17, 205.24, 910, 204.18; 135/42

[56] References Cited

U.S. PATENT DOCUMENTS

| | | | |
|---|---|---|---|
| 1,711,270 | 4/1929 | Litle, Jr. .................. | 138/42 |
| 2,664,109 | 12/1953 | Iager .................. | 138/42 |
| 3,677,267 | 7/1972 | Richards .................. | 138/42 |
| 4,351,329 | 9/1982 | Ellestad et al. .................. | 128/204.21 |
| 4,409,977 | 10/1983 | Bisera et al. .................. | 128/204.21 |
| 4,552,140 | 11/1985 | Cowley et al. .................. | 128/204.25 |

*Primary Examiner*—Edward M. Coven
*Assistant Examiner*—J. P. Lacyk
*Attorney, Agent, or Firm*—Hoffmann & Baron

[57] ABSTRACT

A high-efficiency and compact high-frequency artificial respirator is disclosed. A patient circuit (1) of the artificial respirator is supplied with a respiration gas from a respiration gas supply source (6), and an oscillation generator (2) imparts high-frequency oscillation to the respiration gas thereby supplied. The patient circuit (1) has at one thereof a chamber defined by a vessel (12d) or a serpentine passage (31). A positive pressure is exerted on the chamber as a result of the gas being injected from nozzles (12e, 32).

10 Claims, 4 Drawing Sheets

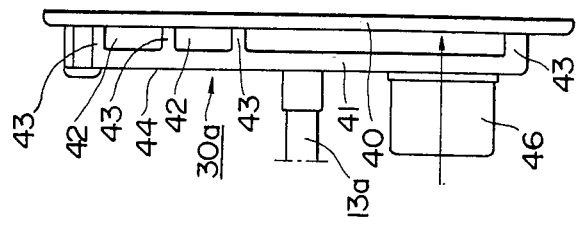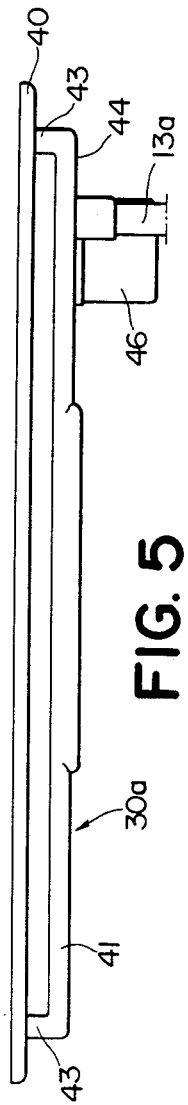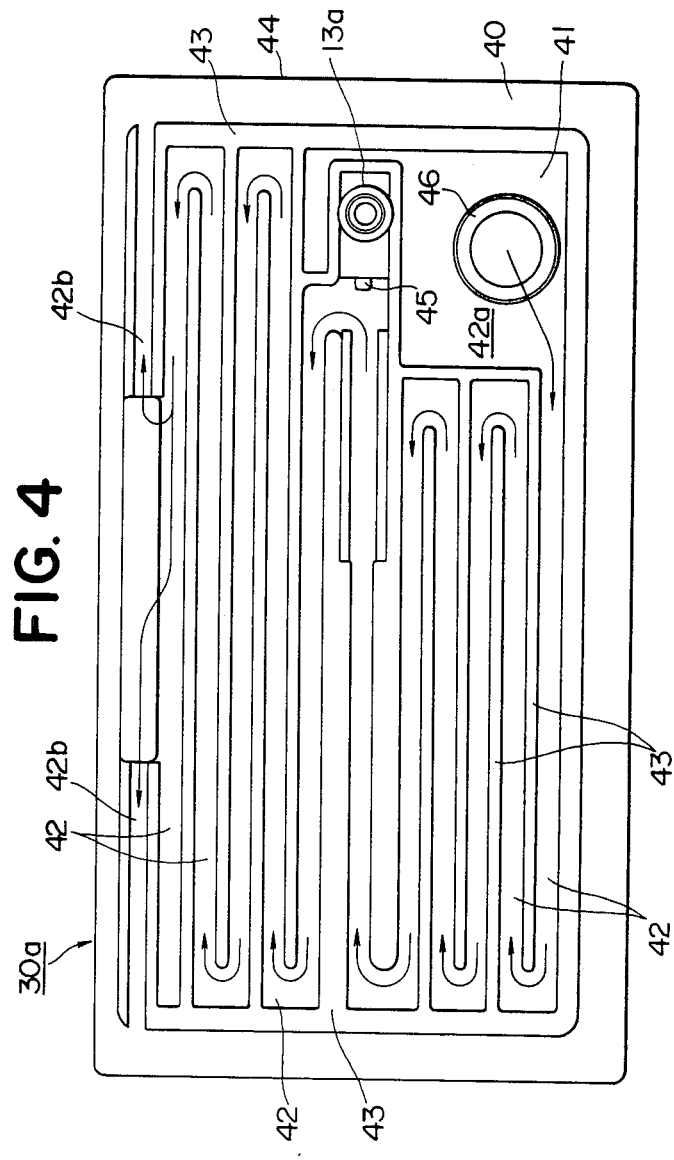

HIGH-FREQUENCY ARTIFICIAL RESPIRATOR

This is a continuation of application Ser. No. 890,020, filed July 14, 1986 abandoned.

TECHNICAL FIELD

The present invention relates to a high-frequency artificial respirator capable of giving artificial respiration by applying a high-frequency oscillation to the gas within the air passages of a patient.

BACKROUND ART

It is known that conventional types of high-frequency artificial respirators have generally been constructed as shown in FIG. 1. In the Figure, a patient circuit generally indicated at 1 is constituted by a tube 1a inserted into the trachea of a patient, three tubes 1b, 1c and 1d being respectively communicated with the tube 1a. One end of the tube 1b is connected to an oscillation generator 2 having a cylinder 2a and a piston 2c driven by a motor 2b, one end of the tube 1c is connected to a pneumatic low-pass filter 3, and one end of the tube 1d connected to a humidification and respiration gas supply pipe 5. In addition, a respiration pressure measurement line 4 is connected to the tube 1b.

The piston 2c is caused to reciprocally move by virtue of the motion of a motor 2b and thereby imparts a high-frequency oscillation, normally of 4 Hz or higher, to the gas flow within the patient circuit 1. In consequence, the diffusion of the gas within the air passages of the patient is accelerated, thereby giving artificial respiration to the patient.

The low-pass filter 3 is constituted by a tube having an internal diameter of about 8 to 10 mm and a length of about 3 to 5 m, and, as shown in FIG. 1, is formed in a spiral manner so as to reduce the space occupied by it to the minimum. Since the low-pass filter 3, as mentioned above, has a relatively small diameter and, in addition, a length of 3 to 5 m, when a gas abruptly starts to flow through the filter 3, resistance acts upon the gas flow in the filter 3, thereby preventing the abrupt flow of gas from being discharged to the exterior. Accordingly, the low-pass filter 3 allows slowly flowing components such as the continuous flow based on the respiration spontaneously performed by the patient and a gas supplied to the patient to pass, but precludes the passage of a high-frequency oscillation component generated by the oscillation generator 2.

A respiration gas supply source 6 is connected to the distal end of the humidification and respiration gas supply pipe 5 through a solenoid valve 7, a flowmeter 10 with a flow control valve and a humidifier 11 which are arranged in order. The humidifier 11 is provided so as to suitably humidify the respiration gas supplied into the air passages of the patient. A pressure sensor 8 is mounted on the distal end of the respiration pressure measurement line 4. The pressure sensor 8 is arranged to detect the gas pressure within the patient circuit 1 and deliver to a controller 9 signals obtained from the detection.

In addition, the controller 9 is electrically connected to the motor 2b and the solenoid valve 7 as well as the above-described pressure sensor 8. The controller 9 controls the opening and closing of the solenoid valve 7 on the basis of the gas pressure within the patient circuit 1 detected by the pressure sensor 8, whereby it is possible to consistently maintain the pressure of a supplied gas (or inner pressure of the patient circuit 1) within a suitable range of pressure.

However, such a conventional type of high-frequency artificial respirator involves the following disadvantages. As mentioned above, the low-pass filter 3 functions to allow only the passage of slowly flowing components such as the continuous flow caused by the spontaneous respiration of the patient and a gas supplied to him/her in order to prevent the loss of high-frequency oscillation components generated by the oscillation generator 2. The low-pass filter 3 having such a function is constituted by a tube having an internal diameter of about 8 to 10 mm and a length of about 3 to 5 m, so that the filter 3 unavoidably takes a fairly large percentage of the space occupied by the entire respirator, thus making it difficult to reduce the overall size of the respirator. Also, an operator uses the artificial respirator with the low-pass filter 3 being normally laid on the floor. For this reason, the operator inadvertently step on the filter 3, and thus, it may occasionally become impossible to maintain the normal operation of the respirator itself.

Accordingly, it is an object of the present invention to provide a high-frequency artificial respirator which can be reduced in size by making the low-pass filter 3 compact.

It is another object of the present invention to provide a high-frequency artificial respirator which can be operated more safely than the prior-art one.

It is a further object of the present invention to provide a high-frequency artificial respirator which can be operated more efficiently than the prior-art one.

It is yet another object of the present invention to provide a high-frequency artificial respirator capable of normally operating with efficiency irrespective of the level of the pressure within the air passages of a patient.

Disclosure of Invention

To these ends, the present invention provides a high-frequency artificial respirator comprising:

a patient circuit for delivering to the air passages of a patient the respiration gas supplied from a respiration gas supply source;

oscillation generating means connected to the patient circuit for imparting high-frequency oscillation to the respiration gas fed into the patient circuit;

a chamber communicated with the patient circuit, having an opening so formed as to open into the outside air; and a nozzle disposed in the vicinity of the opening so that the gas supplied from the gas supply source may be injected through the opening into the chamber, thereby generating positive pressure within the chamber.

The above-described construction is not exclusive. For example, the chamber may be constituted by a vessel having at its bottom a hole communicated with the patient circuit, or having a serpentine tube at its one end which is connected to the patient circuit. In a case where the chamber includes such a serpentine tube, the above-mentioned nozzle may be disposed at an intermediate portion of the serpentine tube. In addition, a gas supply control means may be provided at a location between the gas supply source and the nozzle. In this case, the gas supply control means may be controlled on the basis of the output of an additional pressure detecting means for detecting the gas pressure within the patient circuit.

BRIEF DESCRIPTION OF THE DRAWINGS

FIG. 4 is a diagrammatic plan view of a modification of a positive pressure generation unit incorporated into the high-frequency artificial respirator shown in FIG. 3;

FIG. 5 is a diagrammatic front elevational view of the positive pressure generation unit shown in FIG. 4; and FIG. 6 is a diagrammatic side view of the positive pressure generation unit shown in FIG. 4.

BEST MODES FOR CARRYING OUT THE INVENTION

Figure 1:
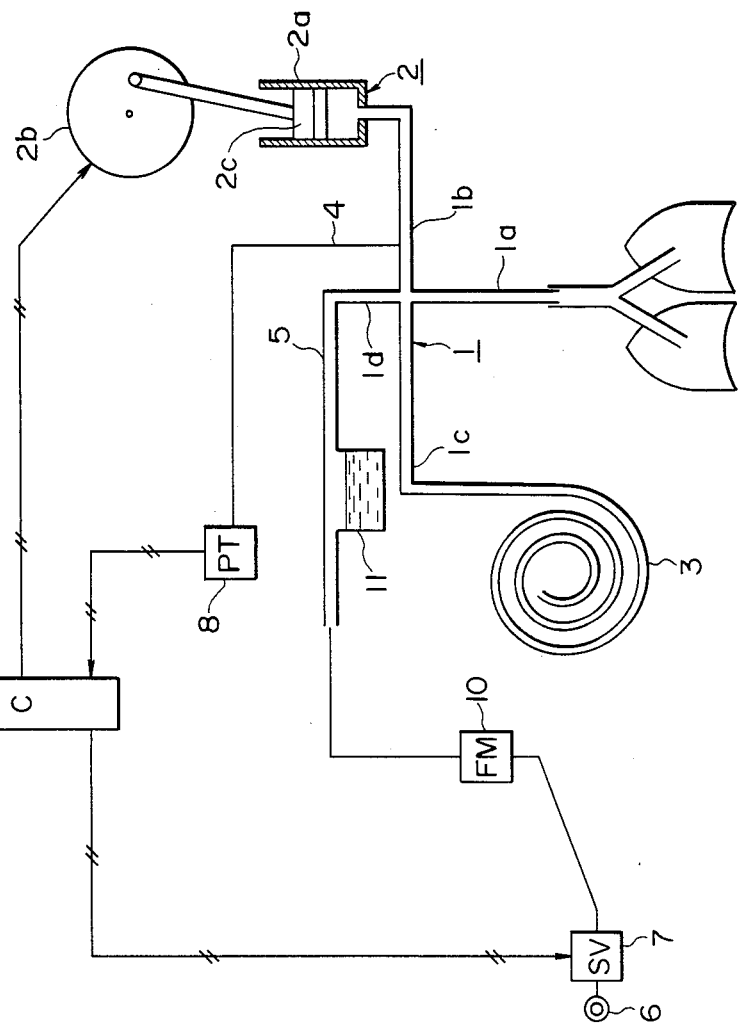
FIG. 1 is a block diagram schematically showing the construction of the prior-art high-frequency artificial respirator.
Figure 2:
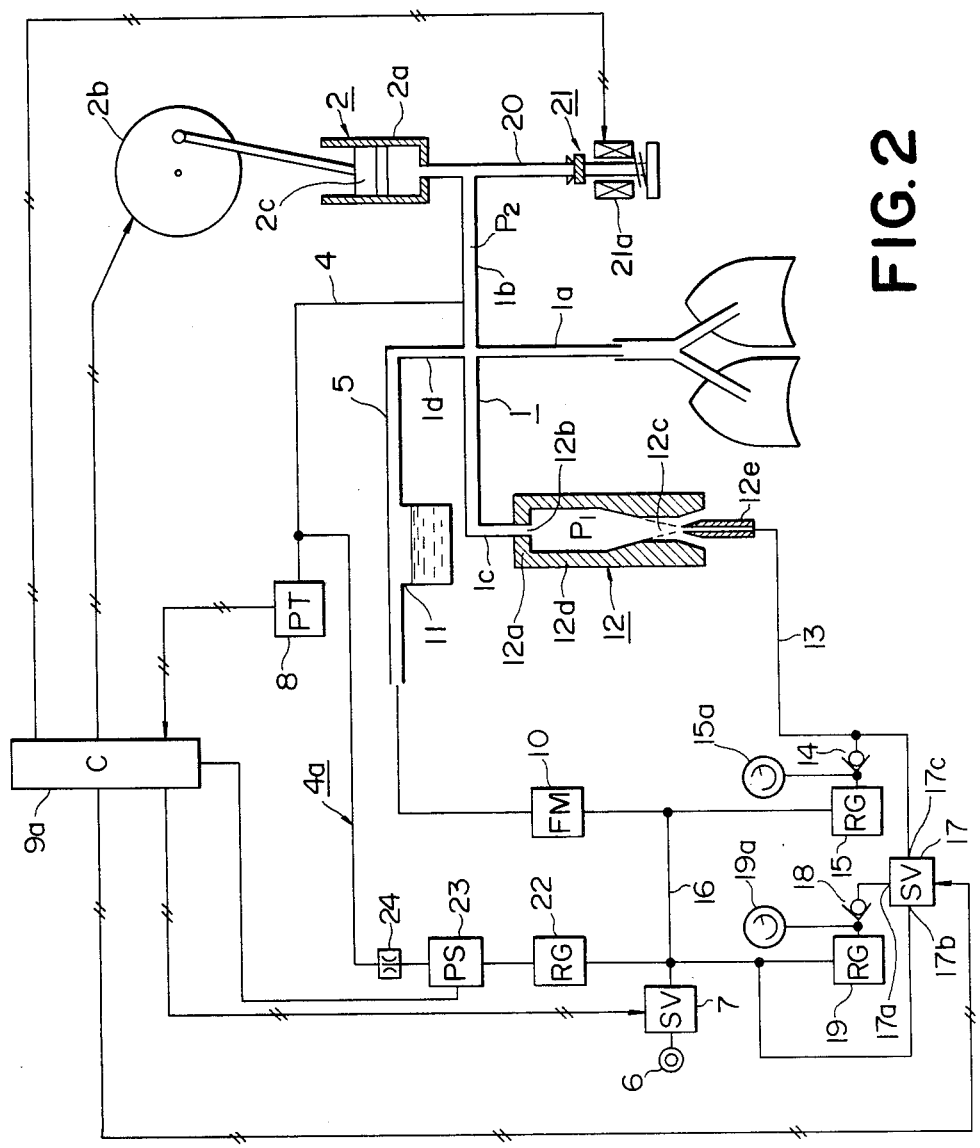
FIG. 2 is a block diagram schematically showing a first embodiment of the high-frequency artificial respirator in accordance with the present invention.

FIG. 2 shows the first embodiment of the high-frequency artificial respirator of this invention, in which like reference numerals are used for the sake of simplicity to denote like or corresponding elements which constitute each of the components shown in FIG. 1. In FIG. 2, a positive pressure generation unit indicated generally at 12 is constituted by: a cylindrical vessel 12d having a hole 12b formed at a bottom 12a, the interior of the vessel 12d being communicated with the tube 1c through the hole 12b, and a small-diameter opening 12c being formed on the side opposite to the bottom 12a; and a nozzle 12e which is disposed in the proximity of the opening 12c, with the injection tip placed toward the interior of the vessel 12d (or chamber). As shown, the opening 12c of the vessel 12d is formed large enough to ensure that the interior of the vessel 12d is adequately communicated with the outside air even when the nozzle 12e is inserted in the opening 12c.

A respiration gas is supplied to a gas supply line 13 connected to the nozzle 12e through any one of the following three routes.

(i) a route constituted by a line 16 connected to the outlet of the solenoid valve 7, a regulator 15 and a check valve 14;

(ii) a route constituted by the line 16, a regulator 19, a check valve 18 and a solenoid valve 17; or (iii) a route constituted by the line 16 and the solenoid valve 17.

The solenoid valve 7 is opened and closed under the control of the controller 9a comprising a microprocessor and so forth, and supplies to the line 16 the respiration gas within the respiration gas supply source 6. The solenoid valve 17 includes a pair of inlets 17a, 17b and a single outlet 17c and, in response to the output of the controller 9a, the valve 17 is adapted to select any one of the three states, viz. the communication between the inlet 17a and the outlet 17c, the communication between the inlet 17a and the outlet 17c, and the closed state. Pressure gauges 15a, 19a monitor the pressure output of the regulators 15, 19.

The pressure output of the regulator 15 and that of the regulator 19 are normally set to desired pressure levels which are different from each other. Therefore, the pressure of the gas supplied to the nozzle 12e can be varied in a stepped manner by selecting any one of the foregoing three routes. As described above, since the gas regulators 15, 19 together with the solenoid valve 17 are provided on the upstream side of the gas supply tube 13, the nozzle 12e can be consistently supplied with a respiration gas having a predetermined pressure level, whereby the internal pressure of the vessel 12d can be consistently maintained at a constant pressure $P_1$ which is lower than the pressure of the gas supplied to the patient circuit 1.

A branch pipe 20 is connected to a point where the oscillation generator 2 is coupled to the patient circuit 1, and one end of the branch pipe 20 is so formed as to open in the outside air. An automatic-operating plug 21 of a solenoid drive type is mounted on the opening of the branch pipe 20 in order to suitably open and close the opening. A solenoid 21a incorporated in the plug 21 is arranged to be driven by means of the controller 9a on the basis of the pressure level detected by the pressure sensor 8, so that the interior of the patient circuit 1 is consistently maintained at a pressure $P_2$ which is higher than the pressure $P_1$ formed within the positive pressure generation unit 12. In consequence, a continuous flow such as the gas flow caused by natural respiration and the steady flow of a specially supplied gas can be smoothly discharged into the outside through the positive pressure generation unit 12.

In this fashion, the positive pressure generation unit 12 serves as a low-pass filter acting upon the patient circuit 1, the unit 12 exerting low resistance with respect to a slowly varied gas flow and also high resistance with respect to a rapidly varied gas flow.

In order to prevent the water or droplets within the patient circuit 1 from invading the pressure sensor 8 through the pressure measurement line 4, a protection circuit 4a is disposed between the output line 16 of the solenoid valve 7 and the pressure sensor 8. A gas regulator 22, a pressure switch 23 and a resistor 24 are arranged in that order from the upstream side of the circuit 4a to the downstream side thereof. The gas regulator 22 is provided so as to consistently maintain the gas supply pressure at a constant level. The pressure switch 23 is normally preset to a pressure about 10% lower than the pressure generated between the regulator 22 and the resistor 24. If the pressure between the regulator 22 and the resistor 24 is made lower by 10% or greater than this pressure level for any reason, that is, if a gas fails to flow normally from the regulator 22 to the pressure sensor 8, the pressure switch 23 issues an alarm signal under control of the controller 9a.

The vessel 12d of the positive pressure generation unit 12 connected to the tube 1c of the patient circuit 1 is formed in such a manner that one end opens into the outside air. However, since the predetermined positive pressure $P_1$ is loaded on the interior of the vessel 12d due to the gas injected through the nozzle 12e, the high-frequency components do not leak out of the patient circuit 1, thereby preventing attenuation in the level of the high-frequency components. In addition, the positive pressure $P_1$ caused by the injection through the nozzle 12e does not become a hindrance to the continuous flow (pressure: $P_2 > P_2$), so that this continuous flow can be easily discharged into the outside and there is no risk of excessively raising the internal pressure within the air passage of the patient. Since the positive pressure generation unit 12 constituted by the vessel 12d and the nozzle 12e is remarkably compact, all components required for the entire artificial respirator can be integrated into a compact, single unit. Hence, an operator can more safely operate the respirator as compared with the prior-art one.

The second preferred embodiment of the artificial respirator of this invention will be described below with specific reference to FIG. 3.

Figure 3:
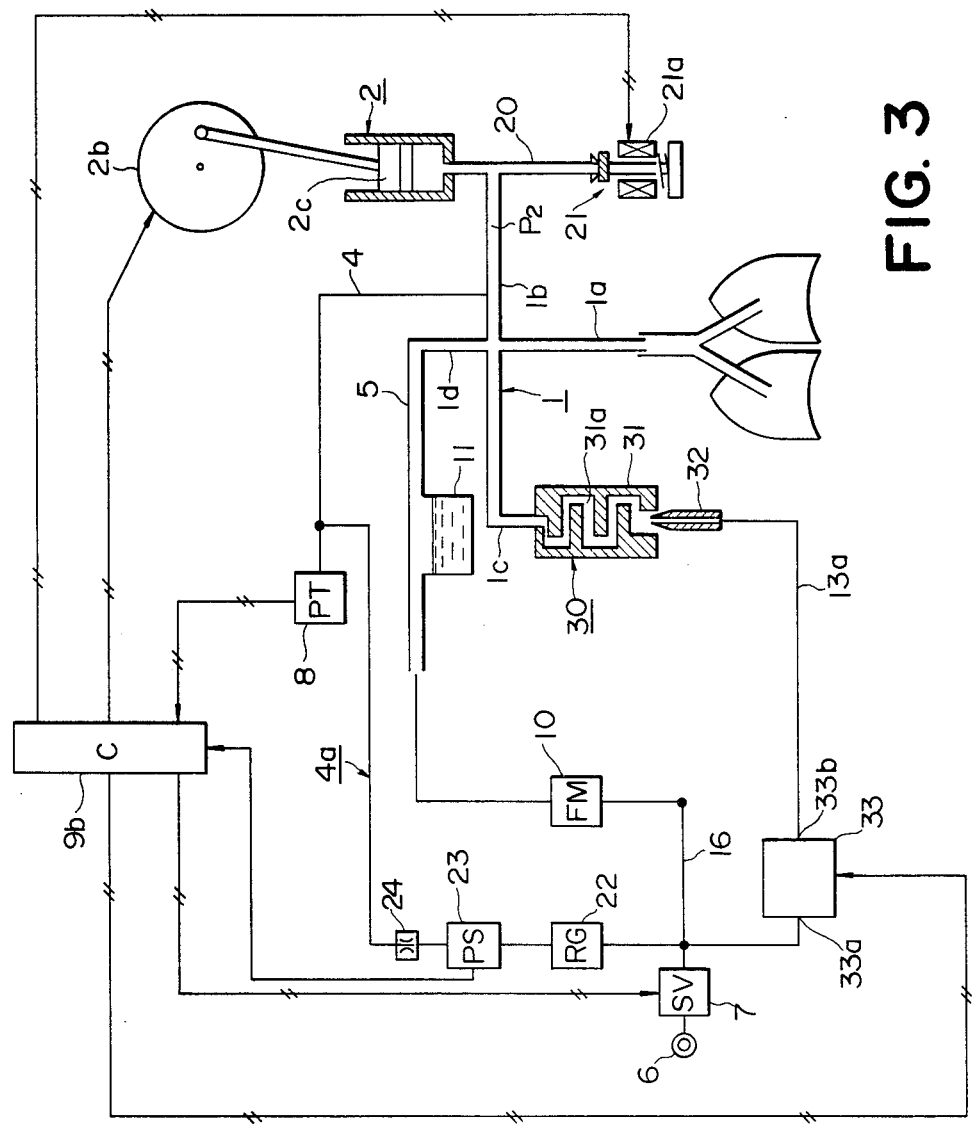
FIG. 3 is a block diagram schematically showing a second embodiment of the high-frequency artificial respirator in accordance with the present invention.

FIG. 3 is a block diagram schematically showing the construction of the second embodiment of the high-frequency artificial respirator of this invention. The artificial respirator shown in this diagram differs from that shown in FIG. 2 in the following respects.

A positive pressure generation unit 30 constituted by a pneumatic resistor 31 and a nozzle 32 is connected to the tube 1c of the patient circuit 1 of the second embodiment of the artificial respirator. The pneumatic resistor 31 is constituted by a serpentine gas passage 31a formed in the interior of the unit 30, with one end of the passage 31a connected to the tube 1c, and the nozzle 32 is disposed at the other end of the gas passage 31a in such a manner that the nozzle tip faces the interior of the passage 31a.

An inlet 33a of a proportional-type solenoid valve 33 is inserted in the line 16 connected to the outlet of the solenoid valve 7, and an outlet 33b of the solenoid valve 33 is connected to the nozzle 32 through a line 13a. Such a proportional-type solenoid valve 33 is a known device which includes an air booster and a bimorph element capable of continuously varying the degree of transformation in proportion to continuous variations in the applied voltage. The solenoid valve 33 is capable of continuously increasing and decreasing the flow rate of a gas toward the nozzle 32 in proportion to continuous changes in the voltage applied from the controller 9b. As an example, an electropneumatic converter made by Syoketsu Kinzoku Kogyo Kabushiki Kaisha, Japan, can be used for such a solenoid valve 33.

According to the above-described arrangement, since the gas passage 31a constituting the resistor 31 of the positive pressure generation unit 30 is formed with a serpentine shape and has a long passage length, the high-frequency oscillation within the patient circuit 1 is not easily transmitted to the outside, that is, leakage of the high-frequency oscillation component is substantially prevented. As a result, it is possible to reduce the space required for the positive pressure generation unit 30, and in addition, an improvement can be accomplished in the efficiency with which the high-frequency oscillation component is prevented from leaking out of the patient circuit 1.

As will be understood from the foregoing description, the proportional-type solenoid valve 33 comprising an air booster, a piezoelectric element (or bimorph element) and so forth, is capable of continuously (analogously) varying the flow of air in correspondence with continuous changes in the output of supplied electric signals. Hence, a single valve 33 of this kind can be substituted for a multiplicity of valves. The controller 9b is further arranged to analogously control the opening of the valve 33 on the basis of the output of the pressure sensor 8, and thereby continuously regulate the flow rate of the gas supplied to the resistor 31 in correspondence with changes in the variable average pressure within the air passages, whereby it is possible to easily maintain the average air passages internal pressure in the air passages at a constant level.

A modification of the positive pressure generation unit 30 will be described below with reference to FIGS. 4 through 6.

As shown in FIGS. 4 through 6, a modified positive pressure generation unit 30a is constituted by: a resistor 44 including a bottom plate 40, a top plate 41 and partition walls 43 defining a serpentine gas passage 42 interposed between the plates 40 and 41; and a nozzle 45 which is disposed at a certain position within the gas passage 42 and which has an injection tip positioned in the direction opposite to that of the gas flow indicated by each arrow. The line 13a shown in FIG. 3 is connected to the nozzle 45. One end 42a on the upstream side of the gas passage 42 has a connection 46 to which the tube 1c of the patient circuit 1 is connected. The other end 42b on the downstream side of the gas passage 42 is so formed as to open into the atmosphere.

According to the positive pressure generation unit 30a, the serpentine gas passage 42 is further formed on the downstream side of the nozzle 45, thereby exhibiting the proper characteristics of a low-pass filter.

What is claimed is:

1. A high-frequency artificial respirator comprising:
   a patient circuit for delivering a first respiration gas to an air passage of a patient, the first respiration gas being supplied from a respiration gas source;
   oscillation generation means connected to said patient circuit for imparting a high-frequency oscillation to said first respiration gas in said patient circuit;
   means for low-pass filtering slowly varying gas components, said means for low-pass filtering including an essentially closed chamber having one input opening for connection with said patient circuit and having one circuit in communication with ambient atmosphere; and
   means for positive pressure generation being interfaced and communicating with said means for low-pass filtering slowly varying gas components, said means for positive pressure generation including a nozzle disposed in the vicinity of said one output opening in said chamber, for injecting a second gas through said output opening into said chamber to thereby generate a positive pressure within said chamber.

2. A high-frequency artificial respirator according to claim 1, wherein said chamber is defined by a cylindrical vessel having said input opening communicated with said patient circuit at a bottom thereof and a mouth serving as said output opening, said nozzle injecting said gas into said vessel through said mouth.

3. A high-frequency artificial respirator according a claim 1, wherein said chamber is defined by a serpentine passage communicated with said patient circuit at one end thereof and with ambient atmosphere at the other end thereof, said nozzle injecting said gas into said serpentine passage through said other end.

4. A high-frequency artificial respirator according to claim 1, wherein said chamber is defined by a serpentine passage communicated with said patient circuit at one end thereof and with ambient atmosphere at the other end thereof, said nozzle being disposed within said serpentine passage intermediate said one and the other ends thereof for injecting said second gas in the direction of said one end of said serpentine passage, which direction is opposite to that of the flow of air exhaled by the patient.

5. A high-frequency artificial respirator according to claim 1 further comprising a gas supply-amount control means interposed between a source of said second gas and said nozzle.

6. A high-frequency artificial respirator according to claim 5, wherein said gas supply-amount control means comprises a plurality of gas regulators selectively interposed between said gas source and said nozzle.

7. A high-frequency artificial respirator according to claim 5, wherein said gas supply-amount control means comprises a proportional-type solenoid valve.

8. A high-frequency artificial respirator according to claim 7 further comprising:
pressure detecting means for detecting a pressure of said respiration gas within said patient circuit; and
control means for driving said proportional-type solenoid valve in accordance with an output of said pressure detecting means to thereby maintain an average pressure of said respiration gas within said patient circuit at a constant level.

9. A high-frequency artificial respirator comprising:
a patient circuit for delivering a first respiration gas to an air passage of a patient, the first respiration gas being supplied from a respiration gas source;
oscillation generation means connected to said patient circuit for imparting a high-frequency oscillation to said first respiration gas in said patient circuit;
means for low-pass filtering slowly varying gas components, said means for low-pass filtering including an essentially closed chamber having one input opening for connection with said patient circuit and having one output opening in communication with ambient atmosphere; and
means for positive pressure generation being interfaced and communicating with said means for low-pass filtering slowly varying gas components, said means for positive pressure generation including a nozzle disposed in the vicinity of said one output opening in said chamber, for injecting a second gas through said output opening into said chamber to thereby generate a positive pressure within said chamber, wherein the low-pass filtering means and positive pressure generation means are integrally formed and include a bottom plate, a top plate and partition walls defining a serpentine gas passage interposed between the top and bottom plates, the nozzle of the positive pressure generation means being disposed within the gas passage and having an injection tip positioned in a direction opposite to that of the flow of air exhaled by the patient, the low-pass filtering means and positive pressure generation means further defining the serpentine gas passage with the first open end upstream of the gas passage for connection to the patient circuit and a second open end downstream of the gas passage which is open to the atmosphere, the nozzle being disposed between the first and second open ends of the serpentine passage.

10. A high-frequency artificial respirator comprising:
a patient circuit for delivering a first respiration gas to an air passage of a patient, the first respiration gas being supplied from a respiration gas source;
oscillation generation means connected to said patient circuit for imparting a high-frequency oscillation to said first respiration gas in said patient circuit;
means for low-pass filtering slowly varying gas components, said means for low-pass filtering including an essentially closed chamber having one input opening for connection with said patient circuit and having one output opening in communication with ambient atmosphere;
means for positive pressure generation being interfaced and communicating with said means for low-pass filtering slowly varying gas components, said means for positive pressure generation including a nozzle disposed in the vicinity of said one output opening in said chamber, for injecting a second gas through said output opening into said chamber to thereby generate a positive pressure within said chamber;
a pressure sensor coupled to the patient circuit;
a pressure measurement fluid line coupling the pressure sensor to the patient circuit; and
a circuit for protecting the pressure sensor from moisture within the patient circuit, the pressure sensor protecting circuit including a fluid regulator, a pressure switch and a fluid resistor, the regulator, pressure switch and fluid resistor being coupled together in series and being interposed between the source of gas and the pressure measurement fluid line coupling the pressure sensor to the patient circuit, the pressure sensor protecting circuit providing a constant gas pressure to the pressure measurement fluid line and providing a flow of gas in the pressure measurement fluid line in a direction from the pressure sensor to the patient circuit.

* * * * *